(12) United States Patent
Combs et al.

(10) Patent No.: US 9,167,830 B2
(45) Date of Patent: Oct. 27, 2015

(54) SUBSTITUTED CELLULOSE ACETATES AND USES THEREOF

(75) Inventors: Michael T. Combs, Shady Spring, WV (US); Thomas S. Garrett, Narrows, VA (US)

(73) Assignee: Celanese Acetate LLC, Irving, TX (US)

( * ) Notice: Subject to any disclaimer, the term of this patent is extended or adjusted under 35 U.S.C. 154(b) by 0 days.

(21) Appl. No.: 13/359,568

(22) Filed: Jan. 27, 2012

(65) Prior Publication Data

US 2013/0195787 A1   Aug. 1, 2013

(51) Int. Cl.

| | |
|---|---|
| *A61K 9/14* | (2006.01) |
| *A23G 3/36* | (2006.01) |
| *C08B 5/00* | (2006.01) |
| *A23L 1/39* | (2006.01) |
| *A23L 1/0534* | (2006.01) |
| *A23L 1/06* | (2006.01) |
| *C09K 8/035* | (2006.01) |
| *C09D 101/12* | (2006.01) |
| *C08B 3/06* | (2006.01) |
| *C08B 3/22* | (2006.01) |
| *C08B 5/14* | (2006.01) |

(Continued)

(52) U.S. Cl.
CPC .. *A23G 3/36* (2013.01); *A23G 3/42* (2013.01); *A23L 1/0534* (2013.01); *A23L 1/06* (2013.01); *A23L 1/39* (2013.01); *A61K 8/731* (2013.01); *A61Q 19/00* (2013.01); *C08B 3/06* (2013.01); *C08B 3/22* (2013.01); *C08B 5/00* (2013.01); *C08B 5/14* (2013.01); *C08B 7/00* (2013.01); *C08L 1/12* (2013.01); *C08L 1/16* (2013.01); *C08L 1/20* (2013.01); *C09D 101/12* (2013.01); *C09D 101/16* (2013.01); *C09D 101/20* (2013.01); *C09J 101/12* (2013.01); *C09J 101/16* (2013.01); *C09J 101/20* (2013.01); *C09K 8/035* (2013.01); *C09K 17/40* (2013.01); *A61K 2800/10* (2013.01)

(58) Field of Classification Search
CPC .......................................................... C08B 5/00
See application file for complete search history.

(56) References Cited

U.S. PATENT DOCUMENTS 2,622,079 A * 12/1952 Crane ............................ 536/59
2,639,234 A    5/1953 Morey et al.

(Continued)

FOREIGN PATENT DOCUMENTS

| CN | 101638443 A | 2/2010 |
|---|---|---|
| GB | 1177480 | 1/1970 |

(Continued)

OTHER PUBLICATIONS

International Search Report and Written Opinion for PCT/US2012/056810 dated Apr. 8, 2013.

(Continued)

*Primary Examiner* — Paul Dickinson
(74) *Attorney, Agent, or Firm* — McDermott Will & Emery LLP; Kurt Jones (57) ABSTRACT

The present invention relates to substituted cellulose acetates and methods of use thereof. One embodiment of the present invention provides a drilling fluid having a base fluid and a viscosifier having a substituted cellulose acetate having a polar substituent that comprises an oxygen atom covalently bonded to a nonmetal selected from the group of sulfur, phosphorus, boron, and chlorine; where the nonmetal is present in at least about 0.01% by weight of the substituted cellulose acetate.

20 Claims, 5 Drawing Sheets (51) Int. Cl.

| | | |
|---|---|---|
| C08B 7/00 | (2006.01) | |
| C09D 101/16 | (2006.01) | |
| C09D 101/20 | (2006.01) | |
| C09J 101/12 | (2006.01) | |
| C08L 1/12 | (2006.01) | |
| C08L 1/16 | (2006.01) | |
| C08L 1/20 | (2006.01) | |
| C09J 101/16 | (2006.01) | |
| C09J 101/20 | (2006.01) | |
| C09K 17/40 | (2006.01) | |
| A23G 3/42 | (2006.01) | |
| A61K 8/73 | (2006.01) | |
| A61Q 19/00 | (2006.01) | |

(56) References Cited

U.S. PATENT DOCUMENTS

| | | | |
|---|---|---|---|
| 2,780,228 A | 2/1957 | Touey | |
| 2,848,343 A | 8/1958 | Costello | |
| 3,000,876 A | 9/1961 | Toney et al. | |
| 3,045,006 A | 7/1962 | Gerbeau | |
| 3,075,962 A | 1/1963 | Hiatt et al. | |
| 3,075,963 A | 1/1963 | Hiatt et al. | |
| 3,086,007 A | 4/1963 | Toney et al. | |
| 3,113,674 A | 12/1963 | Kiefer et al. | |
| 3,184,421 A * | 5/1965 | Caldwell et al. | 524/819 |
| 3,335,128 A | 8/1967 | Hiatt et al. | |
| 3,538,079 A | 11/1970 | Steinmann et al. | |
| 3,624,069 A | 11/1971 | Schweiger | |
| 3,702,845 A | 11/1972 | Steigerwald et al. | |
| 3,800,797 A | 4/1974 | Tunc | |
| 3,897,782 A | 8/1975 | Tunc | |
| 3,939,836 A | 2/1976 | Tunc | |
| 3,990,833 A | 11/1976 | Holub et al. | |
| 3,991,021 A | 11/1976 | Roth | |
| 3,994,827 A | 11/1976 | Sakai et al. | |
| 4,005,251 A | 1/1977 | Tunc | |
| 4,039,517 A | 8/1977 | Hamamura et al. | |
| 4,147,603 A | 4/1979 | Pacifici et al. | |
| 4,180,536 A | 12/1979 | Howell, Jr. et al. | |
| 4,238,375 A | 12/1980 | Blount | |
| 4,246,146 A | 1/1981 | Wood et al. | |
| 4,313,857 A | 2/1982 | Blount | |
| 4,336,340 A | 6/1982 | Blount | |
| 4,359,516 A | 11/1982 | Nacci et al. | |
| 4,366,550 A | 12/1982 | Lampe | |
| 4,405,324 A | 9/1983 | Cruz, Jr. | |
| 4,451,638 A | 5/1984 | Blount | |
| 4,590,227 A | 5/1986 | Nakamura et al. | |
| 4,792,357 A * | 12/1988 | Bier | 106/600 |
| 4,837,271 A | 6/1989 | Brindopke | |
| 4,839,254 A | 6/1989 | Pawlowski et al. | |
| 4,983,730 A | 1/1991 | Domeshek et al. | |
| 5,010,156 A | 4/1991 | Cook et al. | |
| 5,591,227 A | 1/1997 | Dinh et al. | |
| 5,595,700 A | 1/1997 | Kitazawa | |
| 5,681,646 A | 10/1997 | Ofosu et al. | |
| 5,711,793 A | 1/1998 | Dannhorn et al. | |
| 5,728,462 A | 3/1998 | Arino et al. | |
| 5,827,852 A | 10/1998 | Russell et al. | |
| 5,913,311 A | 6/1999 | Ito et al. | |
| 5,973,139 A | 10/1999 | Lee et al. | |
| 5,989,689 A | 11/1999 | Komatsu | |
| 6,500,539 B1 | 12/2002 | Chen et al. | |
| 6,599,525 B2 | 7/2003 | Scamilla Aledo et al. | |
| 6,602,994 B1 | 8/2003 | Cash et al. | |
| 6,800,754 B1 | 10/2004 | Chauvelon et al. | |
| 6,989,689 B2 | 1/2006 | Ngai et al. | |
| 7,534,379 B2 | 5/2009 | Ellison et al. | |
| 7,671,193 B2 | 3/2010 | Shibata et al. | |
| 7,863,439 B2 | 1/2011 | Ozaki et al. | |
| 9,023,757 B2 | 5/2015 | Combs et al. | |
| 2002/0052570 A1 | 5/2002 | Naimer | |
| 2002/0096300 A1 | 7/2002 | Yamashita | |
| 2003/0004449 A1 | 1/2003 | Lafratta et al. | |
| 2003/0047190 A1 | 3/2003 | Peele | |
| 2003/0054167 A1 | 3/2003 | Wang | |
| 2003/0143264 A1 | 7/2003 | Margiotta | |
| 2003/0223923 A1 | 12/2003 | Aspinwall et al. | |
| 2004/0077498 A1 | 4/2004 | Lynch | |
| 2005/0187385 A1 | 8/2005 | Nakano et al. | |
| 2005/0287368 A1 | 12/2005 | Corallo et al. | |
| 2007/0167618 A1 | 7/2007 | Wang et al. | |
| 2008/0051502 A1 | 2/2008 | DeRosa et al. | |
| 2008/0156435 A1 | 7/2008 | Kingma et al. | |
| 2008/0202539 A1 | 8/2008 | Banks et al. | |
| 2008/0213597 A1 | 9/2008 | Li | |
| 2009/0000633 A1 | 1/2009 | Lipowicz et al. | |
| 2009/0011033 A1 | 1/2009 | Hauser et al. | |
| 2009/0075107 A1 | 3/2009 | Hedrick et al. | |
| 2010/0291201 A1 | 11/2010 | Shah et al. | |
| 2011/0039694 A1 | 2/2011 | Rosa et al. | |
| 2011/0053866 A1 | 3/2011 | Duffield et al. | |
| 2011/0311833 A1 | 12/2011 | Parker et al. | |
| 2013/0192613 A1 | 8/2013 | Combs et al. | |
| 2013/0195960 A1 | 8/2013 | Combs et al. | |
| 2013/0196063 A1 | 8/2013 | Combs et al. | |
| 2013/0196849 A1 | 8/2013 | Combs et al. | |
| 2015/0037377 A1 | 2/2015 | Combs et al. | |

FOREIGN PATENT DOCUMENTS

| | | |
|---|---|---|
| JP | 2002003773 A | 1/2002 |
| JP | 2002115079 A | 4/2002 |
| JP | 2006079827 A | 3/2006 |
| JP | 2008258013 A | 10/2008 |
| KR | 20060098865 A | 9/2006 |
| KR | 20090084914 A | 8/2009 |
| WO | WO02088288 A1 | 11/2002 |
| WO | 2006095021 A1 | 9/2006 |
| WO | 2009086141 A2 | 7/2009 |
| WO | 2013112497 A1 | 8/2013 |
| WO | 2013112505 A1 | 8/2013 |

OTHER PUBLICATIONS

International Search Report and Written Opinion for PCT?US2012/056819 dated Apr. 8, 2013.

Puls et al., "Degradation of Cellulose Acetate-Based Materials: A Review," J. Polym Environ (2011) 19:152-165.

Baumann et al., "Carbohydrate Polymers as Adhesives," Handbook of Adhesive Technology, 2nd Edition, New York, Marcel Dekker, 2003, pp. 495-510.

Suflet et al., "Phosphorylation of Polysaccharides: New Results on Synthesis and Characterisation of Phosphorylated Cellulose," Reactive & Functional Polymers 2006, vol. 66, pp. 1240-1249.

International Search Report and Written Opinion for PCT/US2013/022616 dated May 15, 2013.

Grinshpan et al., "Cellulose Acetate Sulfate as a Lyotropic Liquid Crystalline Polyelectrolyte: Synthesis, Properties, and Application," International Journal of Polymer Science, vol. 2010, Article ID 831658, 2010.

Luneva et al., Synthesis and Properties of Cellulose Phosphates, Russian Journal of Applied Chemistry, vol. 80, No. 11, pp. 1923-1927 2007.

Official Action for Chinese Patent Application No. 201380006612.5 dated May 15, 2015.

Grinshpan, et al., Cellulose Acetate Sulfate as a Lyotropic Liquid Crystalline Polyelectrolyte: Synthesis, Properties, and Application, Research Article, International Journal of Polymer Science, vol. 2010, Art. ID 831658, 2010.

Official Action for Chinese Patent Application No. 201380006606.X dated Jun. 1, 2015.

* cited by examiner

SUBSTITUTED CELLULOSE ACETATES AND USES THEREOF

BACKGROUND

The present invention relates to synthetic polymers and, in particular, to substituted cellulose acetates, and methods of use thereof.

Cellulose acetate is an acetate ester derivative of cellulose, a naturally occurring biopolymer comprising β-D-glucose monomer units, and is widely used to make a variety of consumer products. Naturally occurring cellulose is insoluble in water and most organic solvents. However, the three free hydroxyl groups of each glucose monomer unit in cellulose can be derivatized to modify certain properties, for example, solubility in certain solvents. Cellulose acetate is thought to be among the most commercially useful derivatives of cellulose, and its specific physical and chemical properties generally depend largely on the degree of substitution of acetate on the three free hydroxyl groups of a glucose monomer unit.

Since its first synthesis, cellulose acetate has been used, among other things, as a film base in photography, a component in adhesives, and a raw material used in the manufacture of cigarette filters. One of the key attributes of cellulose acetate is that it can be processed into many different shapes and forms, including, films, tows, flakes, fibers, and solids, depending on the desirability of the application. For example, cellulose acetate tow is primarily used in the manufacture of cigarette filters.

Most typically, derivatization of cellulose is conducted using acidic catalysts at elevated reaction temperatures. The synthesis of cellulose acetate involves acetylating cellulose, which is commonly obtained from wood pulp, in the presence of acetic anhydride and acids. Acetic acid and sulfuric acid are the two acids usually present during the acetylation reaction. In this reaction, the acetic anhydride serves as the primary acetylating agent; the acetic acid is used primarily as a diluent; and a small amount of the sulfuric acid is used as the catalyst. In general, the monomeric units of cellulose have three hydroxyl groups that are readily available for substitution, e.g., via acetylation. The monomeric units at both ends also have an additional hydroxyl group that are typically involved inter-sugar linkages.

The product of the acetylation reaction is a primary cellulose acetate that usually contains high concentration levels of acetate or, in other words, has a high degree of substitution (DS) of acetate. As used herein, "degree of substitution of acetate" generally refers to the average number of acetates per glucose monomer unit. The structure of cellulose acetate may be generally characterized by specifying the degree of substitution of acetate. Exhaustively acetylated cellulose is commonly referred to as cellulose triacetate, where, according to Federal Trade Commission guidelines, at least 92% of the hydroxyl groups are substituted with acetyl groups. For example, when there are at least about two acetyl groups per cellulose monomer unit (that is, a DS of about 2), the acetyl cellulose can become significantly less biodegradable until at least some of the acetyl groups are removed via chemical or enzymatic hydrolysis. Acetylated cellulose having reduced DS of acetate can be prepared by controlled hydrolysis of cellulose triacetate.

Next, the primary cellulose acetate is hydrolyzed in the presence of acetic acid and sulfuric acid to reduce the DS of acetate of the primary cellulose acetate. The resulting hydrolysis product is usually a cellulose acetate flake having a DS on the order of about 2.4 to about 2.6.

Once cellulose acetate flake is obtained, it may be subjected to further treatment in order to process the cellulose acetate to its desired form. For example, cellulose acetate tow may be formed by dissolving the cellulose acetate flakes in acetone, putting cellulose acetate solution through a series of filtration processes, and dry spinning the acetone dope through microscopic holes in a spinneret. As the cellulose acetate moves through this extrusion process, filaments of cellulose acetate are collected. These filaments are typically bundled and then crimped to ensure tow band cohesion as well as desired bulk. The end result is a cellulose acetate tow, which is essentially a continuous band composed of several thousand filaments held loosely together by crimp. The cellulose acetate tow filaments usually are very thin and may be packed together tightly to create a filter.

As used herein, "cellulose acetate tow" generally refers to post-synthesis processed bundles of filaments of cellulose acetate.

Figure 1:
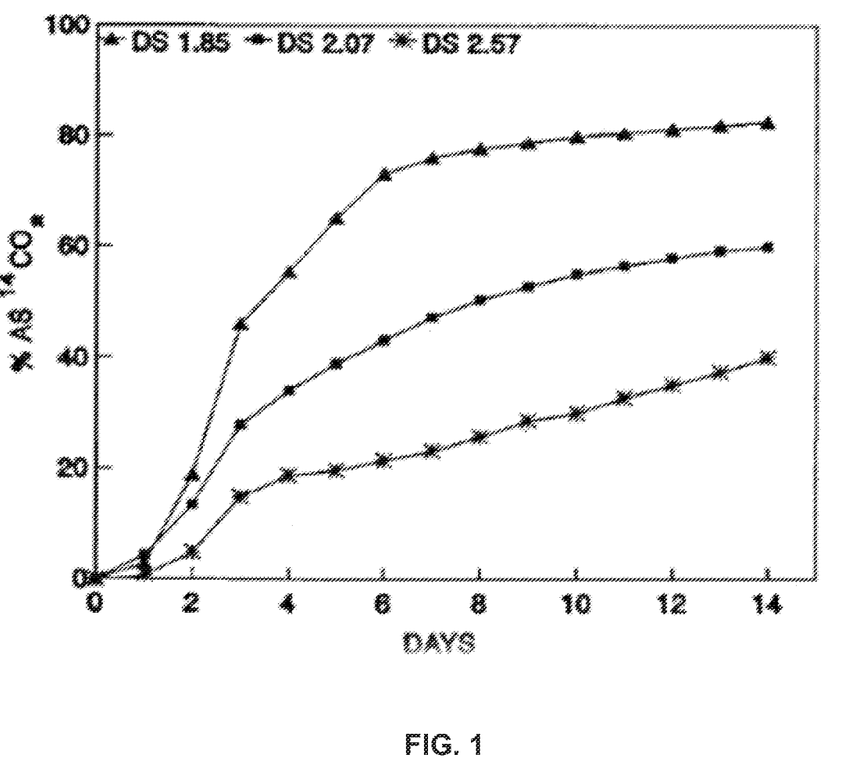
FIG. 1 shows a biodegradability plot of cellulose acetate with varying degrees of substitution.

Cellulose acetate is also environmentally friendly in that it is a readily degradable material made largely from a renewable source, wood pulp. While cellulose acetates that vary in their DS of acetate are structurally similar, this variation can have some effect on the biodegradability of the cellulose acetate. At higher degrees of acetyl substitution, the rate of biodegradation can be significantly reduced relative to naturally occurring cellulose or cellulose having less acetyl substitution. Cellulose acetates having a lower DS of acetate biodegrade more readily than cellulose acetates having a higher DS of acetate. This trend is believed to taper off at lower DS of acetate values because the material becomes insoluble in water. In one example, the biodegradation rates of cellulose acetate having DS values of 1.85, 2.07, and 2.57 were tested for their biodegradability (FIG. 1). The cellulose acetate with a DS of 1.85 showed the highest biodegradation rate while the cellulose acetate with an acetyl value of 2.57 showed the slowest biodegradation rate.

While cellulose acetate is a versatile composition with many commercial uses, the properties of certain cellulose acetate derivatives have not been exhaustively studied. For example, in a typical synthesis, residual sulfate groups are typically removed in order to improve thermal stability. As a result, cellulose acetates synthesized by typical means will have about 0.005% or less of sulfur atoms by weight. As such, there are potential derivatives of cellulose acetate that may provide enhanced properties for many of the consumer applications of cellulose acetate.

SUMMARY OF THE INVENTION

The present invention relates to synthetic polymers and, in particular, to substituted cellulose acetates, and methods of use thereof.

In some embodiments, the present invention provides diapers comprising: an inner layer comprising an absorbent core comprising a substituted cellulose acetate comprising a polar substituent that comprises an oxygen atom covalently bonded to a nonmetal selected from the group consisting of: sulfur, phosphorus, boron, and chlorine; wherein the nonmetal is present in at least about 0.01% by weight of the substituted cellulose acetate; and an outer layer.

In other embodiments, the present invention provides bandages comprising: an absorbent layer comprising a substituted cellulose acetate comprising a polar substituent that comprises an oxygen atom covalently bonded to a nonmetal selected from the group consisting of: sulfur, phosphorus, boron, and chlorine; wherein the nonmetal is present in at least about 0.01% by weight of the substituted cellulose acetate; and a strip is designed to place the absorbent layer in contact with a wound.

In still other embodiments, the present invention provides potting soil compositions comprising: an organic compost; and an absorbent composition comprising a substituted cellulose acetate comprising a polar substituent that comprises an oxygen atom covalently bonded to a nonmetal selected from the group consisting of: sulfur, phosphorus, boron, and chlorine; wherein the nonmetal is present in at least about 0.01% by weight of the substituted cellulose acetate.

In still other embodiments, the present invention provides amended soil compositions comprising: a soil composition; and a water retention additive comprising a substituted cellulose acetate comprising a polar substituent that comprises an oxygen atom covalently bonded to a nonmetal selected from the group consisting of: sulfur, phosphorus, boron, and chlorine; wherein the nonmetal is present in at least about 0.01% by weight of the substituted cellulose acetate.

In still other embodiments, the present invention provides articles comprising: a nonwoven layer that comprises fibers from a substituted cellulose acetate comprising a polar substituent that comprises an oxygen atom covalently bonded to a nonmetal selected from the group consisting of: sulfur, phosphorus, boron, and chlorine; wherein the nonmetal is present in at least about 0.01% by weight of the substituted cellulose acetate.

In still other embodiments, the present invention provides methods comprising: providing a substituted cellulose acetate comprising a polar substituent that comprises an oxygen atom covalently bonded to a nonmetal selected from the group consisting of: sulfur, phosphorus, boron, and chlorine; wherein the nonmetal is present in at least about 0.01% by weight of the substituted cellulose acetate; and placing the substituted cellulose acetate in an absorbent article.

In still other embodiments, the present invention provides methods comprising: providing an absorbent material comprising a substituted cellulose acetate comprising a polar substituent that comprises an oxygen atom covalently bonded to a nonmetal selected from the group consisting of: sulfur, phosphorus, boron, and chlorine; wherein the nonmetal is present in at least about 0.01% by weight of the substituted cellulose acetate; and placing the absorbent material in a diaper.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modification, alteration, and equivalents in form and function, as will occur to those skilled in the art and having the benefit of this disclosure.

DETAILED DESCRIPTION

The present invention relates to synthetic polymers and, in particular, to substituted cellulose acetates, and methods of use thereof.

The present invention provides compositions, methods, and processes related to substituted cellulose acetates that have a number of advantageous and/or desirable properties. The substituted cellulose acetates of the present invention may be utilized in a variety of applications including a number of consumer products, especially where absorbency, adhesiveness, and/or degradability, may be useful.

As used herein, the term "substituted cellulose acetate" generally refers to a cellulose acetate that has at least one polar substituent substituted on the hydroxyl group of a cellulose polymer. As used herein, a "polar substituent" is a non-acetyl chemical moiety comprising an electronegative atom (e.g., oxygen) bonded to a nonmetal (e.g., sulfur, phosphorus, boron, and chlorine) atom.

It has been surprisingly discovered according to the present invention that substituted cellulose acetate composition having relatively high weight percentage of at least one nonmetal atom corresponding to a polar substituent having a relatively high degree of substitution can be provided. Moreover, it has also been surprisingly discovered, that the percentage weight of nonmetal atoms, may be adjusted and/or modified to yield or enhance various properties of substituted cellulose acetate as described herein.

The substituted cellulose acetates of the present invention are, in some embodiments, versatile (i.e., possess many distinct desirable chemical and physical properties) and environmentally friendly (i.e., made from renewable sources, degradable, biodegradable, etc.) materials suitable for use in a number of consumer products.

As used herein, "degradable" refers to the ability of a material to decompose and/or break down into simpler parts. As used herein, "biodegradable" refers to the ability of a material to degrade by the action of living things. Depending on the application, the definition of "biodegradable" may be subject to the results of standard tests, for example, the Organisation for Economic Co-operation and Development (OECD) testing protocols.

Without being limited by theory, it is believed that by adjusting the percentage weight of the nonmetal atom of a polar substituent, a substituted cellulose acetate of the present invention can provide new or enhanced chemical and/or physical properties. For example, it is believed that certain polar substituents (e.g., sulfate) can increase the hydrophilicity of the substituted cellulose acetate as well as increase the potential for electrostatic interaction.

The substituted cellulose acetate compositions, which are described in more detail hereinafter, have certain advantageous properties and commercial roles (e.g., as an adhesive, chemical stabilizer, absorbent) that may be imparted or enhanced based on the percentage weight of nonmetal atom present. In some embodiments, tuning the percentage weight of the nonmetal atom may remove or reduce an undesirable quality or property in the substituted cellulose acetate.

A substituted cellulose acetate may be described by the concentration of its polar substituents which, in turn, may be specified in terms of degree of substitution of the polar substituent (i.e., average number of substituent per glucose monomer unit) or as a percentage weight of the nonmetal (e.g., sulfur, phosphorus, boron, and chlorine) atom present relative to the total weight of the substituted cellulose acetate. In practical terms, modifying the degree of substitution of a polar substituent will also modify the percentage weight of the nonmetal atom on a substituted cellulose acetate by a predictable amount and vice versa. Accordingly, it may be assumed that increasing the degree of substitution of a polar substituent will generally increase the percentage weight of the nonmetal atom present on a substituted cellulose acetate. Conversely, decreasing the degree of substitution of a polar substituent will generally decrease the percentage weight of the nonmetal atom present in a substituted cellulose acetate by a predictable amount.

In theory, the percentage weight of the nonmetal atom in a substituted cellulose acetate may range from about 0.01% to about 25%, which corresponds to a cellulose acetate that has few polar substituents (in some cases, significantly and surprisingly more than typically prepared cellulose acetate) and a cellulose acetate that has been exhaustively substituted. While the present invention is preferably practiced by specifying the percentage weight of the nonmetal of the polar substituent, the present invention may be equivalently practiced by specifying the degree of substitution of the polar substituent or other similar measures of concentration. The degree of substitution of a polar substituent may range from about 0.005 to about 3.

Various embodiments described herein utilize substituted cellulose acetate having a polar substituent in a wide range of consumer products. By adjusting the percentage weight of the nonmetal atom of the polar substituent, it is believed that the substituted cellulose acetate compositions of the present invention may be used, among many things, as an effective absorbent, an adhesive, a chemical stabilizer, and a stabilizing film forming agent. For example, by adjusting the percentage weight of a sulfur atom (e.g., of a sulfate substituent), the substituted cellulose acetate of the present invention may go from a water-soluble material to a water-swellable material. In some embodiments, the water-swellable substituted cellulose acetate composition may be used as a degradable coating to encapsulate, for example, a pharmaceutical composition so that the release of the pharmaceutical composition is delayed in the body. Other properties that may be adjusted include, but are not limited to, solubility in certain solvents, ability to stabilize emulsions, adhesiveness to various surfaces, and biodegradability. These properties may be further adjusted by modifying the percentage weight of the nonmetal atom of the polar substituent present in the substituted cellulose acetate as needed. A person of ordinary skill in the art should be able to modify the percentage weight of nonmetal as necessary in order to practice the many embodiments of the present invention.

In some embodiments, modifying the degree of substitution of acetate may also yield or enhance certain properties of the substituted cellulose acetate. In some embodiments, the water-soluble substituted cellulose acetate has a degree of substitution of acetate between about 0.4 to about 1. In some embodiments, the water-swellable substituted cellulose acetate has a degree of substitution of acetate between about 1 to about 2. As the degree of substitution of acetate is varied between 0.05 to 3, the appropriate solvent system may change. In some embodiments, at the relatively lower degree of substitution of acetate, water is an appropriate solvent. In some embodiments, at the relatively higher degree of substitution of acetate, an organic solvent is required. The degree of substitution may be varied so that a solvent system can be selected that is appropriate to the targeted end use.

In some embodiments, the degree of substitution of a polar substituent may be kept relatively fixed while the degree of substitution of acetate is adjusted. In some embodiments, the combination of adjusting the degree of substitution of polar substituent and degree of substitution of acetate provides the substituted cellulose acetate with the desired properties. In some embodiments, the range of degree of substitution of polar substituent may affect the range of degree of substitution of acetate that is needed to provide the substituted cellulose acetate with the desired properties. In some embodiments, the range of degree of substitution of acetate may affect the range of degree of substitution of polar substituent that is needed to provide the substituted cellulose acetate with the desired properties.

The potential commercial uses of substituted cellulose acetate of the present invention are wide ranging and include, but are not limited to, household articles such as buttons, glasses, linings, blouses, dresses, wedding and party attire, home furnishings, draperies, upholstery, slip covers, and the like. Other commercial uses include filters including cigarette, ink reservoirs, playing cards, and the like, and high absorbency products such as diapers and surgical products.

In some embodiments, as an absorbent, the substituted cellulose acetates of the present invention have a water absorption capacity several times (for example, from about 8 times to about 24 times) its weight in an aqueous-based fluid (e.g., water, saline solution, etc.) depending on the percentage weight of the nonmetal atom present on the substituted cellulose acetate.

In some embodiments, the substituted cellulose acetates of the present invention may be effective as an adhesive, able to glue a variety of substrates including, but not limited to, cardboard, plastic, paper, glass, wood, hemp, saw dust, composites (e.g., fiber reinforced composites), wood shavings and the like. It is also believed that the substituted cellulose acetates of the present invention may be an effective chemical/colloidal stabilizer, able to stabilize various emulsion mixtures.

In some embodiments, the substituted cellulose acetates of the present invention may be used as a stabilizing film forming agent to promote the formation of film of a given mixture. In some embodiments, the formed film may be clear.

The substituted cellulose acetate may exist in many different forms and be utilized in many different ways. In some embodiments, the substituted cellulose acetate may be fibers, woven fabrics, nonwoven fabrics, tows or tow bands (open or non-open), flakes, foams, emulsions, films, gels, dispersions, solutions, pastes, suspensions, and combinations thereof. In some embodiments, the substituted cellulose acetate may be used as coatings, additives, films, layers, cores, and the like.

In some embodiments, the present invention also provides processes for forming substituted cellulose acetate into various shapes of substituted cellulose acetate (e.g., substituted cellulose acetate tow). These processes typically put the substituted cellulose acetate in a better form to be utilized in certain applications. For example, fibers of substituted cellulose acetate may have the particularly desirable properties of being able to selectively absorb and remove levels of certain organic chemicals; being water-soluble or water-swellable; having a high surface area; and being compatible with dyes. It is also believed that the fibers of substituted cellulose acetate may have resistance to mold and mildew. A substituted cellulose acetate may be particularly desirable in textile applications.

While at least some embodiments relate to cellulose acetates having at least one polar substituent, derivatives of cellulose acetates having at least one polar substituent may also be used in accordance with any of the compatible embodiments of the present invention. Derivatives of cellulose acetate may include, but are not limited to, cellulose acetate esters, cellulose acetate mixed esters, and the like. Suitable examples of cellulose acetate esters include, but are not limited to, cellulose acetate propionates, cellulose acetate butyrates, and the like. The degree of esterification of the cellulose acetate esters will depend, at least in part, on the particular application and will be apparent to those of ordinary skill in the art.

The substituted cellulose acetate of the present invention may be characterized by having a polar substituent that comprises an oxygen atom covalently bonded to a nonmetal selected from the group consisting of: sulfur, phosphorus, and boron; wherein the nonmetal is present in at least 0.01% by weight of the substituted cellulose acetate. In some embodiments, the nonmetal may be present in no more than about 25% by weight of the substituted cellulose acetate. Without being limited by theory, it is believed the upper limit of 25% by weight corresponds to a fully substituted cellulose derivative (e.g., sulfate). The exact range of nonmetal weight percentage will depend on, among other things, the chemical makeup of the polar substituent.

Generally, at least a portion of hydroxyl groups on a substituted cellulose acetate will be substituted by acetate. In some embodiments, the degree of substitution of acetate will be from about 0.05 to about 3, preferably from about 0.4 to about 2. In some embodiments, the ratio of degree of substitution of acetate to degree of substitution of polar substituent may be adjusted to produce or enhance the desired property of a substituted cellulose acetate of the present invention. In some embodiments, the DS of acetate is higher than the DS of the polar substituent.

Optionally, the substituted cellulose acetate may further comprise or be mixed with a plasticizer. Suitable examples of plasticizers include, but are not limited to, glycerin, glycerin esters (including mono, di or triacetyl glycerin and glycerin esters), polyethylene glycol, diethylene glycol, propylene glycol, dimethyl sulfoxide, glycerol triacetate, triethylene glycol diacetate, derivatives thereof, combinations thereof, and mixtures thereof. In some embodiments, the plasticizer comprises a plasticizer selected from the group consisting of esters of saturated dibasic acids, esters of saturated polyhydric alcohols, fatty acid esters, sulfonamide resins, derivatives thereof, and combinations thereof. Plasticizers may be added to the substituted cellulose acetate in order to lower the glass transition temperature ($T_g$) and the melting point of the composition. Plasticizers typically function to facilitate processing and to increase the flexibility and toughness of the final product. It is also believed that certain plasticizers (e.g., ether ester, simple ester type, etc.) may increase the capacity of substituted cellulose acetate filters for phenol removal which is a useful property in cigarette filters.

In some embodiments, the polar substituent may be selected from the group consisting of sulfates, phosphates, borates, carbonates, and combinations thereof. In some embodiments, the polar substituent is present in at least about 0.03% by weight of the substituted cellulose acetate. In some embodiments, the nonmetal of the polar substituent is present in no more than about 75% by weight of the substituted cellulose acetate. The exact range of polar substituent weight percentage will depend on, among other things, the chemical makeup of the polar substituent.

In one or more embodiments, the substituted cellulose acetate may have properties that may be imparted or enhanced by increasing or decreasing the concentration of polar substituents or nonmetal atoms. In some embodiments, the substituted cellulose acetate may be water-soluble. In some embodiments, the substituted cellulose acetate may be water-swellable. In some embodiments, the substituted cellulose acetate may be water resistant. In some embodiments, it may be desirable for the substituted cellulose acetate to have a relatively high sulfur percentage and a relatively high degree of substitution for acetate. In particular, water-swellable materials are often marked by their ability to absorb water and are used as water-stopping material, water-retaining material, material supplies, and the like. In some embodiments, the substituted cellulose acetate may be degradable. In some embodiments, the substituted cellulose acetate may be biodegradable.

The substituted cellulose acetate of the present invention may be utilized as an absorbent material for a number of consumer applications. The present invention provides, in some embodiments, diapers comprising an absorbent core comprising the substituted cellulose acetate of the present invention and an outer layer. Optionally, the diaper may further comprise a distribution layer designed to transfer wetness to the absorbent core and/or an outer shell that covers at least a portion of the absorbent core.

In some embodiments, the distribution layer is interposed between the absorbent core and the outer layer. In some embodiments the distribution layer may be waterproof.

In some embodiments, the outer layer surrounds the absorbent core. In some embodiments, the outer layer is waterproof. In some embodiments, the outer layer is configured to receive an insertion of the absorbent core. The outer layer may also be colored or feature ornamental designs that increases the visual attractiveness of the diaper. In some embodiments, the outer layer is configured with an opening to receive an insertion of an absorbent core. In some embodiments, the outer layer may be reusable.

In some embodiments, the outer layer is made from a material comprising a material selected from the group consisting of polyethylene, nonwoven film, composite film, cloth, and combinations thereof.

In some embodiments, the diaper may be disposable. In some embodiments, at least a portion of the diaper may be reusable.

The present invention provides, in some embodiments, bandages comprising an absorbent layer comprising a substituted cellulose acetate of the present invention and a strip designed to maintain the absorbent layer in contact with a wound. Optionally, the absorbent layer further comprises an active ingredient selected from the group consisting of antibiotics, analgesics, antipyretics, antimicrobials, antiseptics, antiallergies, anti-acne, anesthetics, anti-inflammatories, hemostats, cosmetics, vitamins, vasodilators, emollients, pH regulators, antipruritics, counterirritants, antihistamines, steroids, and combinations thereof.

In some embodiments, the antiseptic may comprise at least one transition metal. Suitable examples of a transition metal include, but are not limited to, aluminum, nickel, copper, zinc, titanium, iron, and silver.

In some embodiments, the wound is an incision, a laceration, an abrasion, a puncture wound, a penetration wound, or any combinations of these.

In some embodiments, the strip may be elastic. In some embodiments, the strip may be adhesive. In some embodiments, the strip comprises a material selected from the group consisting of: woven fabric, nonwoven fabric, plastic, latex, and combinations thereof.

In some embodiments, the cigarette filter materials of the present invention comprise a segmented filter or a section of a filter comprising a substituted cellulose acetate of the present invention. In some embodiments, the cigarette filter materials of the present invention further comprise a conventional secondary cellulose diacetate. Optionally, the cigarette filter materials further comprise a plasticizer. Without being limited by theory, it is believed that the substituted cellulose acetate should increase the degradability of the cigarette filter material.

Suitable examples of plasticizers for use with cigarette filter material related embodiments include phthalate, acetyl triethyl citrate, triethyl citrate, acetyltributyl citrate, dibutylsebacate, triacetin, glyceryl triacetate, polyethylene glycol, propylene glycol, and glycerin.

In some embodiments, the substituted cellulose acetate may be a tow. In some embodiments, the substituted cellulose acetate is formed in a rod shape.

In some embodiments, the smoking devices of the present invention comprise a smokeable substance and a cigarette filter that comprises a substituted cellulose acetate filament of the present invention. As used herein, a "smokeable substance" includes anything (e.g., tobacco) that may be burned and its smoke can be tasted or inhaled. Tobaccos may be utilized in any number of different forms including, but not limited to, dried, fermented, cured, cut, and the like.

In some embodiments, a smoking device may comprise a cigar, a pipe, a cigarette, a vaporizer, and the like.

In some embodiments, the coated seeds of the present invention comprise a seed that is coated with a coating that comprises a substituted cellulose acetate of the present invention. Optionally, the coated seeds further comprise a secondary growth augmentation coating. Suitable examples of secondary growth augmentation coating may be selected from the group consisting of primary nutrients, secondary nutrients, hormones, insecticides, pesticides, herbicides, fungicides, bactericides, pigments, binders, surfactants, glidants, and combinations thereof.

Suitable examples of primary nutrients for use in conjunction with some embodiments of the present invention may include, but are not limited to, ammonium nitrate, urea, ammonium phosphate, ammonium sulfate, urea phosphate, ammonium molybdate, potassium nitrate, potassium phosphate, potassium hydroxide, potassium sulfate, and potassium chloride.

Suitable examples of secondary nutrients are selected from the group consisting of magnesium sulfate, calcium nitrate, sodium borate, magnesium nitrate, chelated complex of copper, calcium, iron, zinc, magnesium, manganese, ammonium molybdate, sodium molybdate, benzoic acid, and salicylic acid.

Suitable examples of binders for use in conjunction with some embodiments of the present invention may include, but are not limited to, methylcellulose, carboxymethylcellulose, hydroxymethylcellulose, hydroxypropylcellulose, polyvinyl alcohol, polyvinyl acetate, povidone, copolyvidone, derivatives thereof, and combinations thereof.

Suitable examples of surfactants for use in conjunction with some embodiments of the present invention may include, but are not limited to, lecithin, sodium lauryl sulfate, polysorbate 60, polysorbate 80, polyoxethylene polyoxypropylene block copolymer, derivates thereof, and combinations thereof.

Suitable examples of pigments for use in conjunction with some embodiments of the present invention may include, but are not limited to, titanium dioxide, iron oxide, natural pigments, natural dyes, FD&C colorants, D&C lakes, derivatives thereof, and combinations thereof.

Suitable examples of glidants for use in conjunction with some embodiments of the present invention may include, but are not limited to, talc, colloidal silicon dioxide, stearic acid, derivatives thereof, and combinations thereof.

Suitable examples of herbicides for use in conjunction with some embodiments of the present invention may include, but are not limited to, glyphosate, dicamba, alanchlor, meolachlor, oxabetrinil, thiocarbamate 5-ethyl-N,N-dipropyl-thiocarbamate, acetochlor, derivatives thereof, and combinations thereof.

Suitable examples of antidotal compounds for use in conjunction with some embodiments of the present invention may include, but are not limited to, fluorazole, cyometrinil, N,N-diallyl dichloroacetamide, derivatives thereof, and combinations thereof.

Suitable examples of fungicide, bactericide, insecticide, and pesticide for use in conjunction with some embodiments of the present invention may include, but are not limited to, inorganic coppers, organic coppers, heavy metal compounds, propenoic acids, oximine ethers, substituted oximine ethers, derivatives thereof, and combinations thereof.

Suitable examples of plant hormones for use in conjunction with some embodiments of the present invention may include, but are not limited to, auxins, gibberellic acids, cytokines, derivatives thereof, and combinations thereof.

In some embodiments, the coated pharmaceutical compositions of the present invention comprise a pharmaceutical composition that is coated with a coating that comprises a substituted cellulose acetate of the present invention.

In some embodiments, the pharmaceutical composition for use in conjunction with some embodiments of the present invention may include, but are not limited to, analgesics, anti-inflammatory agents, anti-arrhythmic agents, anti-asthma agents, anti-bacterial agents, anti-viral agents, anti-coagulants, anti-dementia agents, anti-depressants, anti-diabetics, anti-hypertensive agents, anti-malarials, anti-migraine agents, anti-muscarinic agents, anti-neoplastic agents, immunosuppressants, anti-protozoal agents, anti-thyroid agents, anti-tussives, anxiolytics, sedatives, hypnotics, neuroleptics, neuro-protective agents, beta blockers, cardiac inotropic agents, cell adhesion inhibitors, corticosteroids, cytokine receptor activity modulators, diuretics, anti-parkinsonian agents, gastrointestinal agents, histamine H-receptor antagonists, keratolytics, lipid regulating agents, muscle relaxants, nitrates, anti-fungal agents, anti-anginal agents, non-steroid anti-asthma agents, nutritional agents, sex hormones, stimulants, anti-erectile dysfunction agents, anesthetics, antihistamines, decongestants, cough suppressants, demulcents, expectorants, derivatives thereof, combinations thereof, and mixtures thereof.

In some embodiments, the pharmaceutical composition for use in conjunction with some embodiments of the present invention may include, but are not limited to, pseudoephedrine, phenylpropanolamine, phenylephrine, ephedrine, dextromethorphan, chlorphedianol, carbetapentane, caramiphen, noscapine, diphenhydramine, codeine, menthol, hydrocodone, hydromorphone, fominoben, glyceryl guaiacolate, terpin hydrate, ammonium chloride, N-acetylcysteine, bromhexine, ambroxol, chlorpheniramine, brompheniramine, dexchlorpheniramine, dexbrompheniramine, tripolidine, azatadine, doxylamine, tripelennamine, cyproheptadine, hydroxyzine, elemastine, carbinoxamine, phenindamine, bromodiphenhydramine, pyilamine, acrivastine, AHR-11325, astemizole, azelastine, cetirizine, ebastine, ketotifen, lodoxamide, loratidine, levocabastine, mequitazine, oxatomide, setastine, tazifylline, temelastine, terfenadine, terbutaline, atropine, aminophylline, epinephrine, isoprenaline, metaproterenol, bitoterol, theophylline, albuterol, aspirin, acetaminophen, ibuprofen, naproxen, phenol, benzocaine, hexyl resorcinol, dyclonine, derivatives thereof, combinations thereof, the pharmaceutically acceptable salts thereof, and mixtures thereof.

The present invention provides kits for detection of an analyte comprising a reporter molecule that is coated with a coating that comprises a substituted cellulose acetate of the present invention.

The reporter molecule for use in conjunction with some embodiments of the present invention may include, but are not limited to, an antibody, a protein, an enzyme, a peptide, a nucleic acid, a small molecule, a fluorophore, derivatives thereof, and combinations thereof.

In some embodiments, the coating is water-soluble or water-swellable. In general, the coating provides a protective layer that can delay or prevent the degradation (e.g., denaturation, cleavage) of the reporter molecule during storage.

In some embodiments, the coated stents of the present invention comprise a stent having an outer coating layer that comprises a substituted cellulose acetate of the present invention and an inner coating layer that comprises a pharmaceutical composition.

In some embodiments, the stent comprises a shape-memory material. Suitable examples of shape-memory material for use in conjunction with some embodiments of the present invention may include, but are not limited to, zinc alloys, copper alloys, gold alloys, iron alloys, copper-zinc-aluminum-nickel alloys, copper-aluminum-nickel alloys, and nickel-titanium alloys.

In some embodiments, the stent comprises a polymer. Suitable examples of polymer for use in conjunction with some embodiments of the present invention may include, but are not limited to, fibrin, polylactic acid, silicones, polyurethanes, polyesters, vinyl homopolymers, vinyl copolymers, acrylate homopolymers, acrylate copolymers, polyethers, cellulosics, derivatives thereof, and combinations thereof.

In some embodiments, the pharmaceutical composition is selected from the group consisting of: glucocorticoids, heparin, hirudin, tocopherol, angiopeptin, aspirin, growth factors, oligonucleotides, anti-platelet agents, anti-coagulant agents, anti-mitotic agents, anti-oxidants, anti-metabolite agents, anti-inflammatory agents, and combinations thereof.

In some embodiments, the potting soil compositions of the present invention comprise an organic compost and an absorbent composition comprising a substituted cellulose acetate of the present invention. Optionally, the potting soil composition may further comprise at least one component selected from the group consisting of loam, diatomaceous earth component, Perlite component, and combinations thereof.

In some embodiments, loam comprises components selected from the group consisting of sand, silt, clay, and combinations thereof.

In some embodiments, the diatomaceous earth component comprises at least one component selected from the group consisting of diatomaceous earth, phosphate, magnesium, potassium, nitrogen, and combinations thereof.

In some embodiments, the amended soil compositions of the present invention comprise a soil composition and a water retention additive comprising a substituted cellulose acetate of the present invention. Optionally, the amended soil composition may further comprise an additive selected from the group consisting of sand, silt, clay, calcined clay, iron oxide, dry resin, and combinations of these.

Suitable dry resins for use in conjunction with some embodiments of the present invention may include, but are not limited to, acrylic polymer, polyvinyl acetate polymer, vinyl acetate copolymer, derivatives thereof, and combinations thereof.

In some embodiments, the drilling fluids of the present invention comprise a base fluid and a viscosifier comprising a substituted cellulose acetate of the present invention. Optionally, the drilling fluid may further comprise an additive selected from the group consisting of fluid loss control agents, clay inhibitors, lubricants, weighting agents, viscosifiers, and any combinations thereof.

In some embodiments, the base fluid may be an aqueous fluid, an oil-based fluid, a synthetic fluid, or an emulsion.

In some embodiments, the present invention provides articles comprising a nonwoven layer that comprises fibers from a substituted cellulose acetate of the present invention.

In some embodiments, the nonwoven layer may include, but are not limited to, diapers, feminine hygiene products, wet wipes, bandages, disposable towels, disposable slippers, isolation gowns, surgical gowns, surgical drapes and covers, surgical scrub suits, caps, filters (e.g., HEPA filters; water, coffee, tea bags; liquid cartridges, vacuum bags; geotextiles (e.g., geomembranes); carpet backing; and envelopes.

In some embodiments, the present invention provides a process for making a substituted cellulose acetate tow comprising spinning a dope comprising a solution of cellulose diacetate and substituted cellulose acetate of the present invention; and solvent; taking-up the as-spun substituted cellulose acetate filaments; forming a tow from the substituted cellulose acetate filaments; crimping the tow; conditioning the crimped tow; and baling the dried crimped tow. Optionally, the process may further comprise the step of lubricating the substituted cellulose acetate filaments.

In some embodiments, the solvent is water, acetone, methylethyl ketone, methylene chloride, dioxane, dimethyl formamide, methanol, ethanol, glacial acetic acid, supercritical $CO_2$, any suitable solvent capable of dissolving the aforementioned polymers, or any combination thereof. By way of nonlimiting example, a solvent for cellulose acetate may be an acetone/methanol mixture.

In some embodiments, the substituted cellulose acetate is spun in a spinneret. In some embodiments, the spinneret comprises holes. These holes may be of any shape that is compatible with one or more embodiments of the present invention. The spinneret design and/or spinning parameters may affect the rate at which the solvent evaporates from the filament, which may affect the size, cross-sectional shape, strength, and processability of the filaments. In some embodiments, a spinneret may comprise a plurality of holes spaced at least 0.070 inches apart. In some embodiments, spinnerets for use in conjunction with the present invention may comprise a plurality of extrusion holes in a donut configuration. As used herein, "donut configuration" refers to any shape (circular, ovular, polygonal, triangular, and the like) having a void in the middle, wherein the void does not have holes for extrusion. As used herein, the terms "holes" and "extrusion holes," when used in conjunction with a spinnerets design, may be used interchangeably referring generally to openings through which the dope is extruded. In some embodiments, extrusion holes may be tapered, e.g., countersinks, with capillary exits. Tapering may be at a constant angle or at more than one angle. In some embodiments, extrusion holes within a single spinneret may have different tapering angles. In some embodiments, the extrusion holes and/or capillary exits may have a cross-sectional shape that produces a desired filament cross-sectional shape. Examples of extrusion hole and/or capillary exit cross-sectional shapes may include, but not be limited to, circular, substantially circular, ovular, substantially ovular, crescent, multi-lobal, polygonal (e.g., like tripods, tetrapods, stars, triangles, squares, trapezoids, pentagons, hexagons, and so on with sides of even lengths or varying lengths), polygonal with rounded corners, and any hybrid thereof. In some embodiments, a spinneret may comprise at least two different cross-sectional shaped extrusion holes and/or capillary exits. In some embodiments, a spinneret may comprise at least two different size extrusion holes and/or capillary exits. In some embodiments, the size and/or cross-sectional shape of an extrusion hole may vary from that of the corresponding capillary exit.

In some embodiments, the spinning parameters may include extruding filaments at a drawdown ratio (fiber exit speed to take-up speed) ranging from about 0.7 to about 1.6.

It should be understood by one skilled in the art that extruding does not imply a single method or action for producing the filaments and could be interchanged with, at least, spinning, expelling, and the like.

In some embodiments, the methods of the present invention comprise providing substituted cellulose acetate of the present invention and placing the substituted cellulose acetate in an absorbent article. In some embodiments, the absorbent article may be any article (e.g., a garment, a gel, a piece of furniture, etc.) that may utilize an absorbent material. Suitable examples of absorbent articles may include, but are not limited to, diapers, incontinence garments, bandages, surgical pads, hot and cold therapy packs, water beds, artificial snow, and combinations thereof. In some embodiments, the absorbent article is disposable and/or degradable.

In some embodiments, the substituted cellulose acetate may be placed in the inner portion of an absorbent article. In some embodiments, the substituted cellulose acetate may be placed on the outer portion of an absorbent article. In some embodiments, the substituted cellulose acetate may be part of the outer portion of an absorbent article. The term "placing" is not intended to limit the present invention to any specific mode of action.

In some embodiments, the methods of the present invention comprise coating a seed with a coating comprising a substituted cellulose acetate of the present invention. Optionally, the coating may further comprise at least one ingredient selected from the group consisting of a plasticizer, a binder, a wax, a stabilizer, and a colorant.

In some embodiments, methods of the present invention comprise coating a pharmaceutical composition with a coating comprising a substituted cellulose acetate of the present invention. Optionally, the coating may further comprise an additive selected from the group consisting of a plasticizer, an annealing agent, an emulsifying agent, an emulsion stabilizer, and combinations of these.

In some embodiments, the annealing agent comprises a water-soluble polymer selected from the group consisting of hydroxypropyl cellulose, hydroxypropyl methyl cellulose, methyl cellulose, methyl ethyl cellulose, polyvinylpyrrolidone, sodium carboxymethylcellulose, derivatives thereof, and combinations thereof.

In some embodiments, the methods of the present invention comprise providing an adhesive comprising a substituted cellulose acetate of the present invention and applying the adhesive on a surface. In some embodiments, the surface may be selected from the group consisting of wood, plastic, paper, glass, cardboard, and combinations of these. In some embodiments, the adhesive is a dispersion. Optionally, the adhesive may further comprise a solvent and/or an additive.

In some embodiments, the solvent may be aqueous. In some embodiments, the solvent may be a mixture such as an organic/water solvent. In some embodiments, the solvent may be present in about 40% to about 99% by weight of the adhesive.

In some embodiments, the additive comprises an additive selected from the group consisting of multi-valent salts (e.g., zirconium salts such as zirconium carbonate), polyamide epichlorohydrin resins, aldehydes (e.g., glyoxal, gluteraldehyde, hydroxyadipaldehyde), formaldehyde crosslinkers (e.g., zero-formaldehyde, low-formaldehyde crosslinkers), polyvinyl acetates, polyvinyl alcohols, polystyrenes, polylactic acids, derivatives thereof, and combinations thereof.

In some embodiments, the present invention provides a paint composition comprising a pigment and a stabilizing film forming agent that comprises a substituted cellulose acetate of the present invention and coating a surface with the paint. Optionally, the paint may further comprise at least one element selected from the group consisting of: a solvent, a filler, an antifreeze additive, a catalyst, a thickener, an adhesion promoter, a UV stabilizer, a de-glossing agent, a biocide, and combinations thereof.

Suitable examples of solvents include, but are not limited to, an aliphatic solvent, an aromatic solvent, an alcohol, a ketone, a hydrocarbon, an ester, a petroleum distillate, water, derivatives thereof, and combinations thereof.

Suitable examples of pigments include pigments selected from the group consisting of clay, calcium carbonate, mica, silica, talc, titanium dioxide, derivatives thereof, and combinations thereof.

Suitable examples of filters include fillers selected from the group consisting of: diatomaceous earth, talc, lime, barite, clay, derivatives thereof, and combinations of these.

In some embodiments, the present invention provides a method of providing a paint comprising a pigment; and a stabilizing film forming agent that comprises a substituted cellulose acetate comprising a polar substituent that comprises an oxygen atom covalently bonded to a nonmetal selected from the group consisting of: sulfur, phosphorus, boron, and chlorine; wherein the nonmetal is present in at least about 0.01% by weight of the substituted cellulose acetate;

and coating a surface with the paint.

The methods of the present invention comprise providing a stabilizing film forming agent comprising a substituted cellulose acetate of the present invention and adding the stabilizing film forming agent to an emulsion. Suitable examples of emulsion include, but are not limited to, cosmetic product, hair styling product, photographic film, cutting fluid, skin ointment, paste, balm, oil, wax, detergent, beverage, and combinations of these.

The methods of the present invention comprise providing a thickening agent comprising a substituted cellulose acetate of the present invention and adding the thickening agent to a food composition. Suitable food compositions may include, but are not limited to, soups, gravy, desserts, jellies, candies, and the like.

To facilitate a better understanding of the present invention, the following examples of preferred embodiments are given. In no way should the following examples be read to limit, or to define, the scope of the invention.

EXAMPLE 1

Some adhesive compositions comprising substituted cellulose acetate of the present invention were tested for their adhesive properties on various substrates including wood and cardboard using a lap shear test. These results were compared with commercially available glue (e.g., ELMER'S GLUE ALL®). A summary of the results is shown below in Tables 1A and 1B.

TABLE 1A

Lap Shear Test Results

| Description | Solvent System | Drying | Solids (wt %) | Adhesive Formulation Used (g) | Break (KGF) |
|---|---|---|---|---|---|
| Poly(vinyl acetate)-based adhesive (ELMER'S GLUE ALL ®) | emulsion | ambient 1 hr | 54 | 0.0503 | 58.94 |
| Cellulose Acetate Adhesive 1 | aqueous | ambient 1 hr | 10 | 0.0512 | 43.86 |
| Cellulose Acetate Adhesive 2 | aqueous | ambient 2.25 hr | 20 | 0.0515 | >107 |
| Cellulose Acetate Adhesive 3 | aqueous | ambient 2.25 hr | 15 | 0.0506 | >107 |
| Cellulose Acetate Adhesive 4 | mixed organic/aqueous | ambient 2.5 hr | 10 | 0.0506 | >107 |
| Cellulose Acetate Adhesive 2 | aqueous | ambient 2.5 hr | 15 | 0.0498 | >107 |
| Poly(vinyl acetate)-based adhesive (ELMER'S SCHOOL GLUE) | | ambient overnight | 27 | 0.05 | >107 |
| Cellulose Acetate Adhesive 5 | aqueous | 1 hr oven (120° C.) | 10 | 0.0505 | >107 |
| Cellulose Acetate Adhesive 5 | aqueous | 1 hr oven (120° C.) | 10 | 0.0505 | >107 |
| Cellulose Acetate Adhesive 5 | aqueous | 1 hr oven (120° C.) | 10 | 0.0518 | >107 |

TABLE 1B

Lap Shear Test Results

| Description | Newtons | Substrate | Special Treatment | Sulfur (mg/kg) | Results |
|---|---|---|---|---|---|
| Poly(vinyl acetate)-based adhesive (ELMER'S GLUE ALL ®) | 578.003951 | cardboard | | | paper failure |
| Cellulose Acetate Adhesive 1 | 430.119669 | cardboard | | not measured | paper failure |
| Cellulose Acetate Adhesive 2 | >1000 | wood | | 4940 | exceeded load cell capacity |
| Cellulose Acetate Adhesive 3 | >1000 | wood | | 4530 | exceeded load cell capacity |
| Cellulose Acetate Adhesive 4 | >1000 | wood | | 4940 | exceeded load cell capacity |
| Cellulose Acetate Adhesive 2 | >1000 | wood | | 4940 | exceeded load cell capacity |
| Poly(vinyl acetate)-based adhesive (ELMER'S SCHOOL GLUE) | >1000 | wood | | | exceeded load cell capacity |
| Cellulose Acetate Adhesive 5 | >1000 | wood | | 5570 | exceeded load cell capacity |
| Cellulose Acetate Adhesive 5 | >1000 | wood | 1 hr in refrigerator (4° C.) | 5570 | exceeded load cell capacity |
| Cellulose Acetate Adhesive 5 | >1000 | wood | 1 hr in refrigerator (4° C.) | 5570 | exceeded load cell capacity |

Substituted cellulose acetates with high sulfur content in accordance with one or more embodiments of the present invention (batches Cellulose Acetate Adhesive 1-5) were prepared and tested as a wood adhesive using INSTRON® (Model 3366) Lap Shear test. The results, including the amount of sulfur in the solution (mg of sulfur per kg of sulfur), are summarized in Tables 1A and 1B above. Two small wooden blocks were glued together using a 10% aqueous solution of the adhesives and allowed to dry. The resulting blocks were difficult to separate (i.e., none of the blocks broke in the tensile testing setup used). When enough force was applied to separate the blocks, the wood fibers broke which suggests that the substituted cellulose acetate adhesive is as strong as the wood fibers. Substituted cellulose acetate adhesives were also used to glue cardboard. The cardboard was also difficult to separate. Substituted cellulose acetate adhesives were optically clear and have a high gloss which may be desirable in commercial applications. Substituted cellulose acetate adhesives dried in less than 30 minutes at ambient conditions.

This Example shows, among many things, that substituted cellulose acetate with high sulfur content is effective as an adhesive on a variety of substrates.

EXAMPLE 2

This Example describes the synthesis of a sulfate substituted cellulose acetate of the present invention. In the first step, cellulose was acetylated in the presence of acetic anhydride and sulfuric acid. The preparation of cellulose, acetic acid, acetic anhydride and sulfuric acid is similar to the preparation involved in a standard secondary cellulose acetate diacetate production. Next, the reagents were combined to initiate the acetylation reaction. This reaction was allowed to reach completion and then reacted with any excess anhydride by the addition of water. The reaction rate and temperature may be closely monitored and varied to control certain polymer properties.

Next, the acetylated cellulose (i.e., cellulose acetate) was hydrolyzed in the presence of acetic acid without precipitation and subsequent redissolving steps. This reduced the cellulose acetate to the target acetate DS levels by carefully controlling the reaction temperature and time. Water was added as needed to maintain polymer solubility. This produced a sulfate substituted cellulose acetate product having unexpected and surprisingly high sulfur content.

Finally, the solid was precipitated from the solvent system using appropriate dilutant. The product was washed as needed to remove excess solvent and dried to desired solids level.

EXAMPLE 3

In this Example, a water-swellable cellulose acetate (low sulfur content) and substituted cellulose acetate (high sulfur content) were tested for their ability to absorb water using a thermogravimetric analysis (TGA). Each sample was placed in a TGA system and subjected to the following temperatures. The samples were ramped to 110° C. at 20° C./min. The temperature was held at 110° C. for 30 minutes. The temperature was then ramped to 650° C. at 20° C./min. The sample gas was then switched to air and the temperature was held at 650° C. for 30 minutes. In each test run, the cellulose acetate samples were limited to less than 100 mg.

FIGS. 2-5 show the various TGA analysis runs measuring the water absorbency of high sulfate substituted cellulose acetate and low sulfate substituted cellulose acetate.

Figure 2:
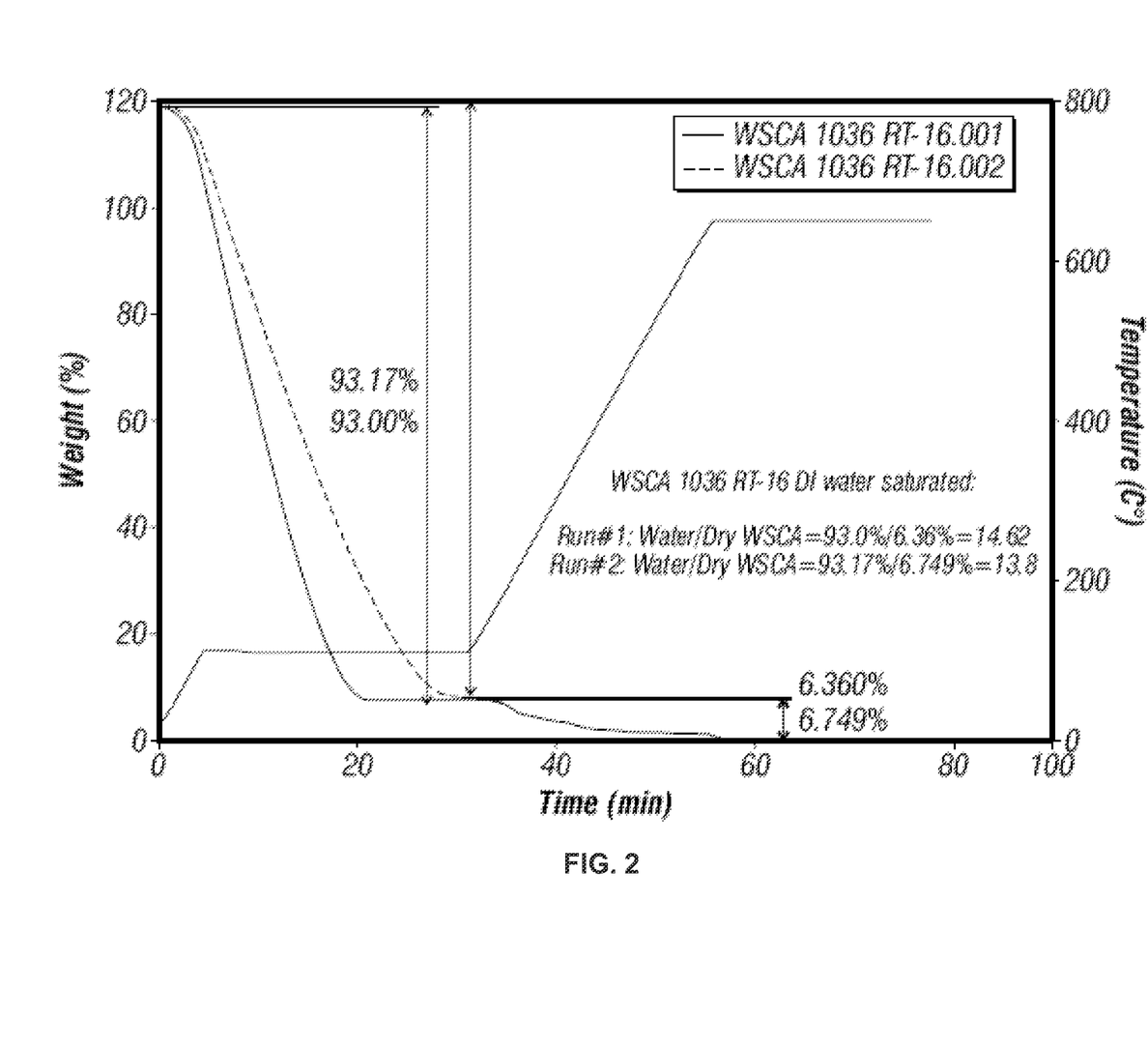
FIG. 2 shows water absorbency data as described in Example 3.

FIG. 2 shows a TGA analysis of water-saturated, water-swellable cellulose acetate (WSCA) 1036 RT-16 dry sample. WSCA 1036 RT-16 is a high sulfate substituted cellulose acetate particulate sample containing approximately 0.5% of sulfur by weight of the cellulose acetate. As temperature is ramped up and held at 110° C., the total weight of the water-saturated sample decreases as the water dried off. The temperature of the TGA system was then ramped to and held at 650° C., thus allowing the high sulfate substituted cellulose acetate to decompose. WSCA 1036 RT-16 was able to absorb approximately 1440% water by weight as the dry sample or over 14 times its weight in water.

Figure 3:
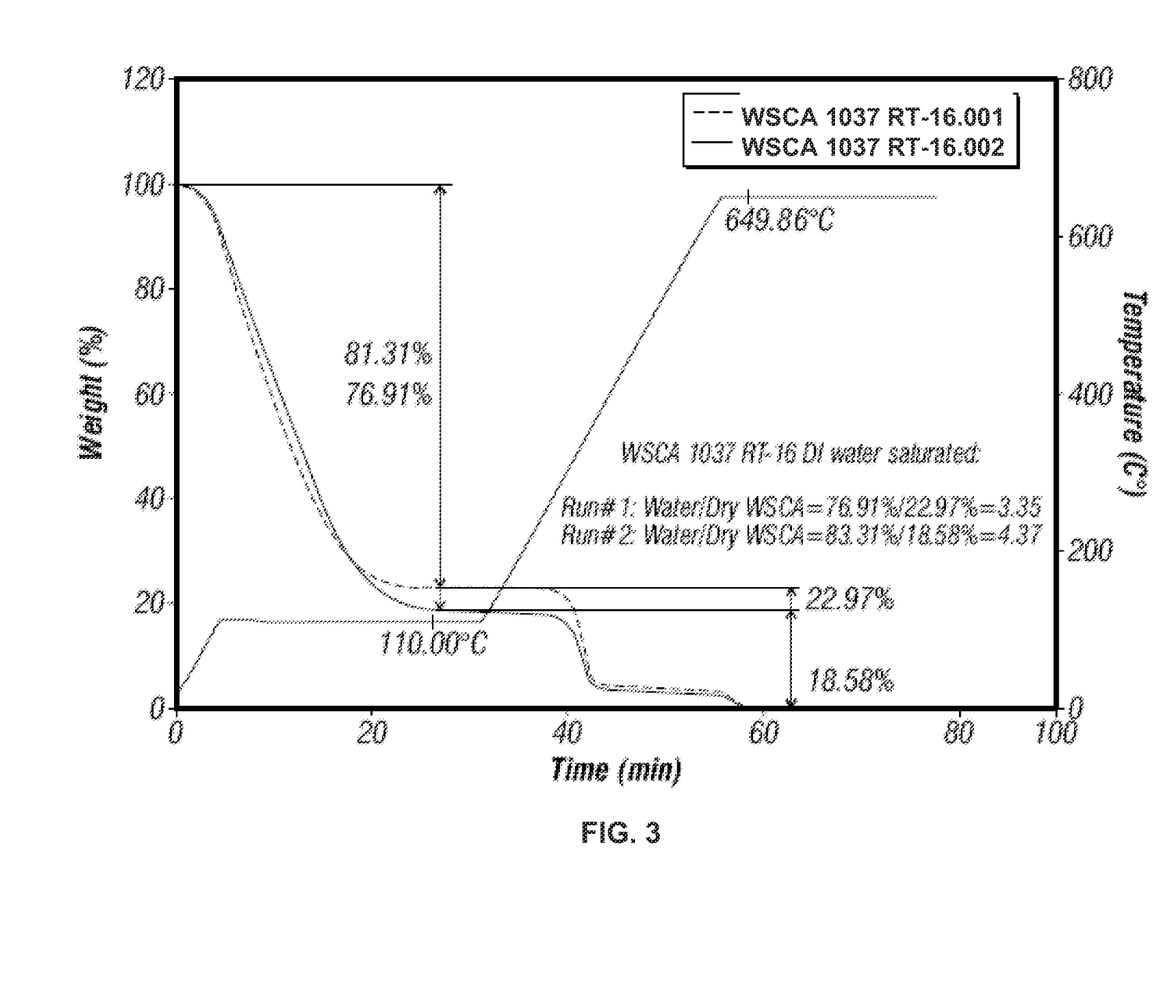
FIG. 3 shows water absorbency data as described in Example 3.

FIG. 3 shows TGA duplicate runs for two WSCA 1037 RT-16 dry samples. Compared to the WSCA 1036 RT-16, the WSCA 1037 RT-16 is a low sulfur substituted cellulose acetate (the DS of acetates are similar). The detected water absorption for the two samples were 76.91% and 81.31%, which corresponds to water to dry WSCA ratios of 3.35 and 4.37 respectively.

Figure 4:
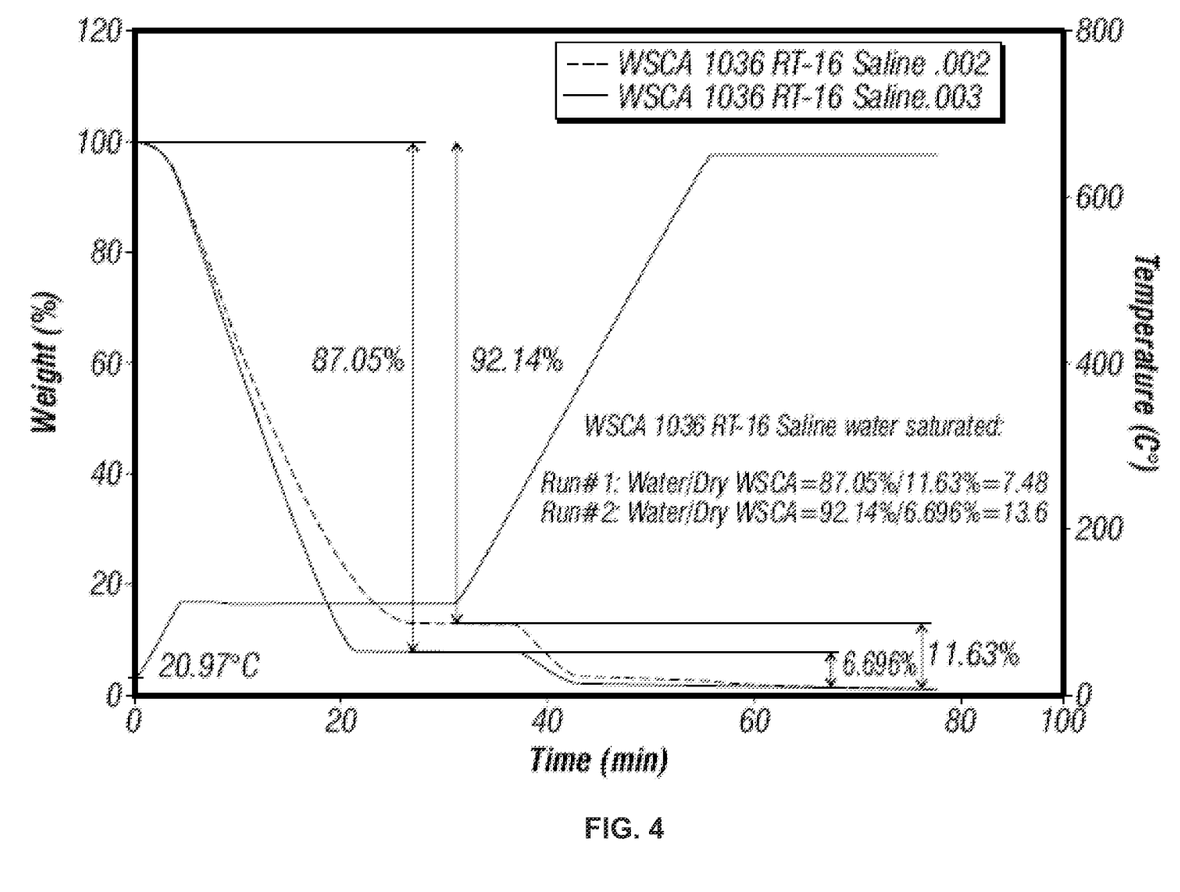
FIG. 4 shows water absorbency data as described in Example 3.

FIG. 4 shows TGA duplicate runs for two saline water (-0.9%) saturated WSCA 1036 (high sulfate) RT-16 samples. The two samples contained 87.05% and 92.14% saline water which corresponded to water to dry WSCA ratios of 7.48 and 13.6 respectively.

Figure 5:
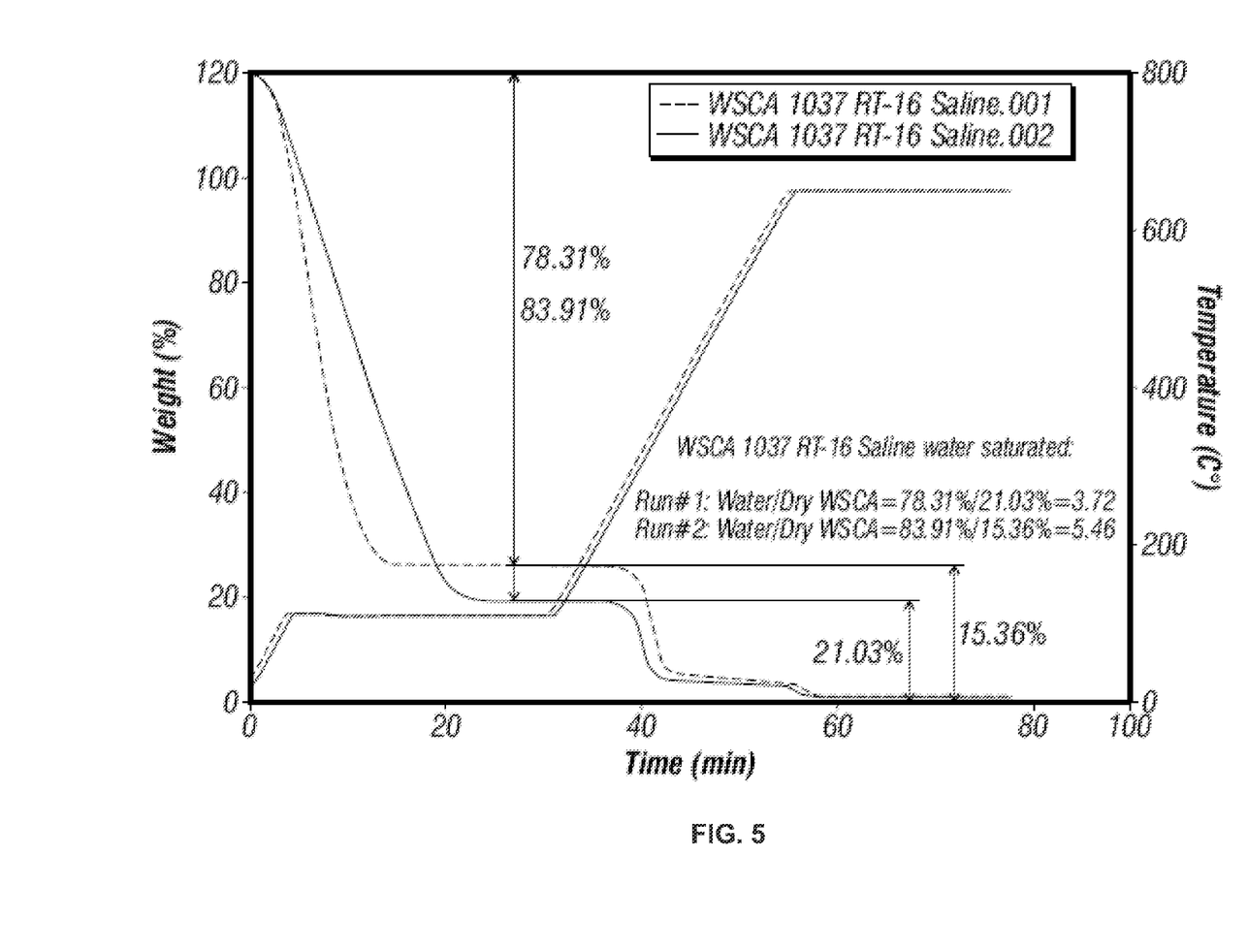
FIG. 5 shows water absorbency data as described in Example 3.

FIG. 5 shows TGA duplicate runs for saline water (~0.9%) saturated WSCA 1037 RT-16 sample. The two samples contained 78.31% and 83.91% saline water which corresponded to water to dry WSCA ratios of 3.72 and 5.46.

This Example shows, among many things, that a substituted cellulose acetate having a high sulfur content is able to absorb water (both deionized and saline) several times its weight. When compared with substituted cellulose acetate with low sulfur content, the high sulfur substituted cellulose acetate displayed superior water (both DI and saline) absorption.

EXAMPLE 4

Various additives were added to some adhesive compositions comprising substituted cellulose acetate of the present invention. The resulting compositions were tested for their adhesive properties on wood substrates (¼" pine strips 1.5" in width) using INSTRON® (Model 3366) Lap Shear test. Summaries of the results are shown below in Tables 2 and 3.

TABLE 2

| Cellulose Acetate Adhesive 6 (620 mg/kg Sulfur) | | | |
|---|---|---|---|
| Zr as % of total solution (% of solids) | Average Break (Kgf)* | Average Break (psi**) | Standard Deviation |
| 0 (0) | 179 | 263 | 32 |
| 0.04% (0.2%) | 271 | 398 | 110 |
| 0.08% (0.4%) | 280 | 411 | 35 |
| 0.16% (0.9%) | 300 | 441 | 71 |
| 0.32% (1.8%) | 362 | 532 | 45 |

*average of 6 replicates
**lap shear of 1.5" × 1" adhered area

TABLE 3

| Cellulose Acetate Adhesives 7-8 | | |
|---|---|---|
| Additive | CA adhesive 7 | CA adhesive 8 |
| No Additive (Kgf at bond break) | 225 | 349 |
| Ammonium Zirconium Carbonate (Kgf at bond break) | 348 | 245 |
| Polyvinyl Acetate MW 140000 (Kgf at bond break) | 271 | 210 |
| Polyvinyl Alcohol MW ~ 150000 (Kgf at bond break) | not tested | 154 |
| Sulfur Levels | 520 mg/kg | 557 mg/kg |

As shown in Tables 2, the addition of zirconium can increase the strength required to break the bond formed by the cellulose acetate adhesive compositions (substituted cellulose acetate with high sulfur content). Table 3 shows results of lap shear testing of cellulose acetate adhesives 7 and 8 with ammonium zirconium carbonate (0.08% Zr), MW 140,000 polyvinyl acetate (14% of solid) and MW 150,000 polyvinyl alcohol (14% of solid). The sulfur content of cellulose acetate adhesives 6, 7, and 8 are 620 mg/kg, 520 mg/kg, and 557 mg/kg respectively.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed:

1. A paint composition comprising:
    a pigment; and
    a stabilizing film forming agent that comprises a substituted cellulose acetate comprising an acetate substituent and a polar substituent that comprises an oxygen atom covalently bonded to a nonmetal selected from the group consisting of: sulfur, phosphorus, boron, and chlorine; wherein a degree of polar substituent substitution is about 0.005 to about 0.02; and wherein a degree of acetate substitution is greater than the degree of polar substituent substitution.

2. The paint composition of claim 1 wherein the nonmetal is present in no more than 25% by weight of the substituted cellulose acetate.

3. The paint composition of claim 1 wherein the pigment comprises a pigment selected from the group consisting of: clay, calcium carbonate, mica, silica, talc, titanium dioxide, and any combination thereof.

4. The paint composition of claim 1 further comprising at least one element selected from the group consisting of: a solvent, a filler, an antifreeze additive, a catalyst, a thickener, an adhesion promoter, a UV stabilizer, a de-glossing agent, a biocide, and any combination of these.

5. The paint composition of claim 4 wherein the solvent comprises a solvent selected from the group consisting of: an aliphatic solvent, an aromatic solvent, an alcohol, a ketone, a hydrocarbon, an ester, a petroleum distillate, water, any derivative thereof, and any combination thereof.

6. The paint composition of claim 4 wherein the filler comprises a filler selected from the group consisting of: diatomaceous earth, talc, lime, barite, clay, any derivative thereof, and any combination thereof.

7. A method comprising:
    providing a paint comprising:
        a pigment; and
        a stabilizing film forming agent that comprises a substituted cellulose acetate comprising an acetate substituent and a polar substituent that comprises an oxygen atom covalently bonded to a nonmetal selected from the group consisting of: sulfur, phosphorus, boron, and chlorine; wherein a degree of polar substituent substitution is about 0.005 to about 0.02; and wherein a degree of acetate substitution is greater than the degree of polar substituent substitution; and
    coating a surface with the paint.

8. The method of claim 7 wherein the nonmetal is present in no more than 25% by weight of the substituted cellulose acetate.

9. The method of claim 7 wherein the pigment comprises a pigment selected from the group consisting of: clay, calcium carbonate, mica, silica, talc, titanium dioxide, and any combination of these.

10. The method of claim 7 wherein the paint further comprises at least one element selected from the group consisting of: a solvent, a filler, an antifreeze additive, a catalyst, a thickener, an adhesion promoter, a UV stabilizer, a de-glossing agent, a biocide, and any combination of these.

11. The method of claim 10 wherein the solvent comprises a solvent selected from the group consisting of: an aliphatic solvent, an aromatic solvent, an alcohol, a ketone, a hydrocarbon, an ester, a petroleum distillate, water, and any combination of these.

12. The method of claim 10 wherein the filler comprises a filler selected from the group consisting of: diatomaceous earth, talc, lime, barite, clay, and any combination of these.

13. The paint composition of claim 1 wherein the degree of acetate substitution is about 0.4 to 3.

14. The paint composition of claim 1 wherein the degree of acetate substitution is about 1 to 3.

15. The paint composition of claim 1 wherein the degree of acetate substitution is about 2 to 3.

16. The paint composition of claim 1 wherein the paint composition is not an emulsion.

17. The paint composition of claim 7 wherein the paint composition is not an emulsion.

18. The paint composition of claim 1 wherein the degree of acetate substitution is about 0.4 to about 1.

19. The paint composition of claim 1 wherein the degree of acetate substitution is about 1 to about 2.

20. A paint composition comprising:
   a pigment; and
   a stabilizing film forming agent that comprises a substituted cellulose acetate comprising an acetate substituent and a polar substituent that comprises an oxygen atom covalently bonded to a nonmetal selected from the group consisting of: sulfur, phosphorus, boron, and chlorine; wherein a degree of polar substituent substitution is about 0.005 to about 0.02; and wherein a degree of acetate substitution is about 0.4 to 3.

* * * * *